US012642679B2

(12) United States Patent
Cho et al.

(10) Patent No.: US 12,642,679 B2
(45) Date of Patent: Jun. 2, 2026

(54) SELF-ALIGNING JOINT ASSISTANCE DEVICE

(71) Applicant: SEOUL NATIONAL UNIVERSITY R&DB FOUNDATION, Seoul (KR)

(72) Inventors: Kyu-Jin Cho, Seoul (KR); Sung Sik Yun, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 18/805,499

(22) Filed: Aug. 14, 2024

(65) Prior Publication Data

US 2024/0398597 A1 Dec. 5, 2024

Related U.S. Application Data

(63) Continuation of application No. PCT/KR2023/001031, filed on Jan. 20, 2023.

(30) Foreign Application Priority Data

Feb. 15, 2022 (KR) ........................ 10-2022-0019508
Dec. 2, 2022 (KR) ........................ 10-2022-0166231

(51) Int. Cl.
*A61F 5/01* (2006.01)
(52) U.S. Cl.
CPC .... *A61F 5/0123* (2013.01); *A61F 2005/0146* (2013.01); *A61F 2005/0155* (2013.01)

(58) Field of Classification Search
CPC ........ A61F 5/01; A61F 5/0102; A61F 5/0104; A61F 5/0106; A61F 5/0109;
(Continued)

(56) References Cited

U.S. PATENT DOCUMENTS 5,857,989 A * 1/1999 Smith, III ............. A61F 5/0123
602/26
2003/0229420 A1 12/2003 Buckingham et al.
(Continued)

FOREIGN PATENT DOCUMENTS

CN 110202549 X 9/2019
CN 110421592 11/2019
(Continued)

*Primary Examiner* — Keri J Nelson
(74) *Attorney, Agent, or Firm* — JCIPRNET

(57) ABSTRACT

The present disclosure relates to a self-aligning joint assistance device and, more particularly, to a self-aligning joint assistance device, wherein the joint assistance device is worn on a joint of the human body, such as the knee joint connecting the thigh and the lower leg, and assists the movement of the joint. The present disclosure provides the advantage of high user friendliness by enabling automatic self-alignment and movement in response to the complex movement of a human joint having a high degree of freedom and providing assistance in the movement of the joint. In addition, the present disclosure has the advantage of having a relatively simple and uncomplicated structure, being able to be fabricated at a relatively low cost, and assisting the function of the joint of a user at a very high degree of freedom in response to the movement of the joint.

20 Claims, 5 Drawing Sheets

(58) Field of Classification Search
CPC .... A61F 5/0111; A61F 5/0118; A61F 5/0123;
A61F 5/0127; A61F 5/013; A61F
2005/0132; A61F 2005/0137; A61F
2005/0141; A61F 2005/0146; A61F
2005/0148; A61F 2005/0151; A61F
2005/0153; A61F 2005/0155; A61F
2005/0169; A61F 2005/0181; A61F
2005/0183
See application file for complete search history.

(56) References Cited

U.S. PATENT DOCUMENTS

| | | | | |
|---|---|---|---|---|
| 2015/0051527 A1* | 2/2015 | Potter | .................. | A61F 5/0125 |
| | | | | 602/16 |
| 2015/0223939 A1 | 8/2015 | Miles et al. | | |
| 2017/0151083 A1 | 6/2017 | Lee et al. | | |
| 2018/0161229 A1* | 6/2018 | Choi | .................. | A61F 5/0123 |
| 2018/0177670 A1 | 6/2018 | Shim et al. | | |
| 2021/0378853 A1 | 12/2021 | Lin et al. | | |
| 2022/0226182 A1 | 7/2022 | Koginov et al. | | |

FOREIGN PATENT DOCUMENTS

| | | |
|---|---|---|
| JP | 2020146762 | 9/2020 |
| KR | 101521784 | 5/2015 |
| KR | 1020160024012 | 3/2016 |
| KR | 20180066715 | 6/2018 |

* cited by examiner

SELF-ALIGNING JOINT ASSISTANCE DEVICE

CROSS-REFERENCE TO RELATED APPLICATION

This application is a continuation of PCT International Application No. PCT/KR2023/001031, filed on Jan. 20, 2023, which claims the priority benefits of Korea application serial no. 10-2022-0019508, filed on Feb. 15, 2022 and Korea application serial no. 10-2022-0166231, filed on Dec. 2, 2022. The entirety of each of the above-mentioned patent applications is hereby incorporated by reference herein and made a part of this specification.

BACKGROUND

Technical Field

The present disclosure relates to a self-aligning joint assistance device and, more particularly, to a self-aligning joint assistance device, wherein the joint assistance device is worn on a joint of the human body, such as the knee joint connecting the thigh and the lower leg, and assists the movement of the joint.

Related Art

Several wearable robotic configurations that may be worn on various joints of the human body, such as the knee joint, to assist the movement of the joint to aid in rehabilitation or ease the movement of users have been developed, but such configurations still remain uncomfortable for users to use.

Taking the knee joint as an example, the tibia not only functions to rotate around the knee joint relative to the femur, but also to move and rotate in a variety of directions and angles relative to the femur. In addition, due to the different joint structures of people, the respective joints have differences in specific movements, i.e., the respective joints move at different angles, relative to each other, and in different directions.

However, it is common for conventional wearable assistance devices to be configured to support simple one-degree-of-freedom rotational motions. Due to the limited degree of freedom, such prior art wearable assistance devices are not able to operate by simulating the complex movements of human joints. Due to the limited number of degrees of freedom, when a user actually wears and moves a wearable assistive device, the movement of the human joint may not be synchronized with the movement of the assistance device, thereby causing pain or discomfort to the user.

Fabricating an assistance device for realizing customized movements by measuring the joint structure of each individual user is time-consuming and expensive, and has the problem that the structure of the assistance device is complex.

Therefore, it would be comfortable for users to readily use a device able to move by adapting to the movement of a joint of an individual and to support the movement of the joint with a high degree of freedom without having to measure the joint structure of the individual or customize the device according to the measured joint structure.

SUMMARY

Technical Problem

The present disclosure is directed to address the need described above, and is intended to provide a self-aligning joint assistance device that has a relatively simple and uncomplicated structure, and is able to adapt to the movement of the joint of a user, move with a high degree of freedom, and provide a force in a direction in which the joint operates to assist the movement of the joint.

Technical Solution

In order to realize the above-described objective, a self-aligning joint assistance device according to the present disclosure is a self-aligning joint assistance device that is worn near a joint connecting a first part and a second part of a human body to assist movement of the joint, the joint assistance device including: a first member worn on the first part, and including a first body, a plurality of first rollers disposed on the first body, and a first sliding portion provided on a lower surface of the first body; a second member worn on the second part, and including a second body, a plurality of second rollers disposed on the second body, and a second sliding portion provided on an upper surface of the second body; an intermediate unit disposed between the first member and the second member, and including an intermediate member disposed between the first member and the second member, a first contact portion provided on the intermediate member to allow mutual sliding while in contact with the first sliding portion of the first member, a second contact portion provided on the intermediate member to allow mutual sliding while in contact with the second sliding portion of the second member, and a plurality of intermediate rollers disposed on the intermediate member; and a wire (or cord) disposed to pass through at least a portion of the plurality of first rollers, the plurality of intermediate rollers, and the plurality of second rollers to provide tension in a direction in which the first member, the intermediate unit, and the second member approach each other so that the first member, the intermediate unit, and the second member mutually slide and are aligned.

In addition, a self-aligning joint assistance device according to the present disclosure is a self-aligning joint assistance device that is worn near a joint connecting a first part and a second part of a human body to assist movement of the joint, the joint assistance device including: a first member worn on the first part, and including a first body, a plurality of first rollers disposed on the first body, and a first sliding portion provided on a lower surface of the first body; a second member worn on the second part, and including a second body, a plurality of second rollers disposed on the second body, and a second sliding portion provided on an upper surface of the second body and configured to allow mutual sliding while in contact with the first sliding portion of the first member; and a wire disposed to pass through at least a portion of the plurality of first rollers and the plurality of second rollers to provide tension in a direction in which the first member and the second member approach each other so that the first member and the second member mutually slide and are aligned.

Advantageous Effects

The present disclosure provides the advantage of high user friendliness by enabling automatic self-alignment and movement in response to the complex movement of a human joint having a high degree of freedom and providing assistance in the movement of the joint.

In addition, the present disclosure has the advantage of having a relatively simple and uncomplicated structure, being able to be fabricated at a relatively low cost, and assisting the function of the joint of a user at a very high degree of freedom in response to the movement of the joint.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Hereinafter, an embodiment of the present disclosure will be described in more detail with reference to the accompanying drawings.

The self-aligning joint assistance device according to the present disclosure is a device that is worn near a joint of the human body to assist the movement of the joint. The self-aligning joint assistance device of the present disclosure may be worn and used on joints of the human body that are connected by ligaments and are able to perform movements such as folding and straightening. In the following, the parts of the human body that are connected to each other by joints and perform a folding motion will be referred to as the first part and the second part, respectively. In addition, a case where the present disclosure is applied to knee joints of the human body will be described below as an example. In the case of the knee joint, the femur (or the thigh) is the first part and the lower leg (or the calf) is the second part.

In such a case where the present disclosure is applied to the knee joint, the straightening of the knee joint is assisted by the tension of a wire or cord, and when the tension of the wire is removed, the knee joint bends under the weight thereof or the muscle strength of the lower leg.

Figure 1:
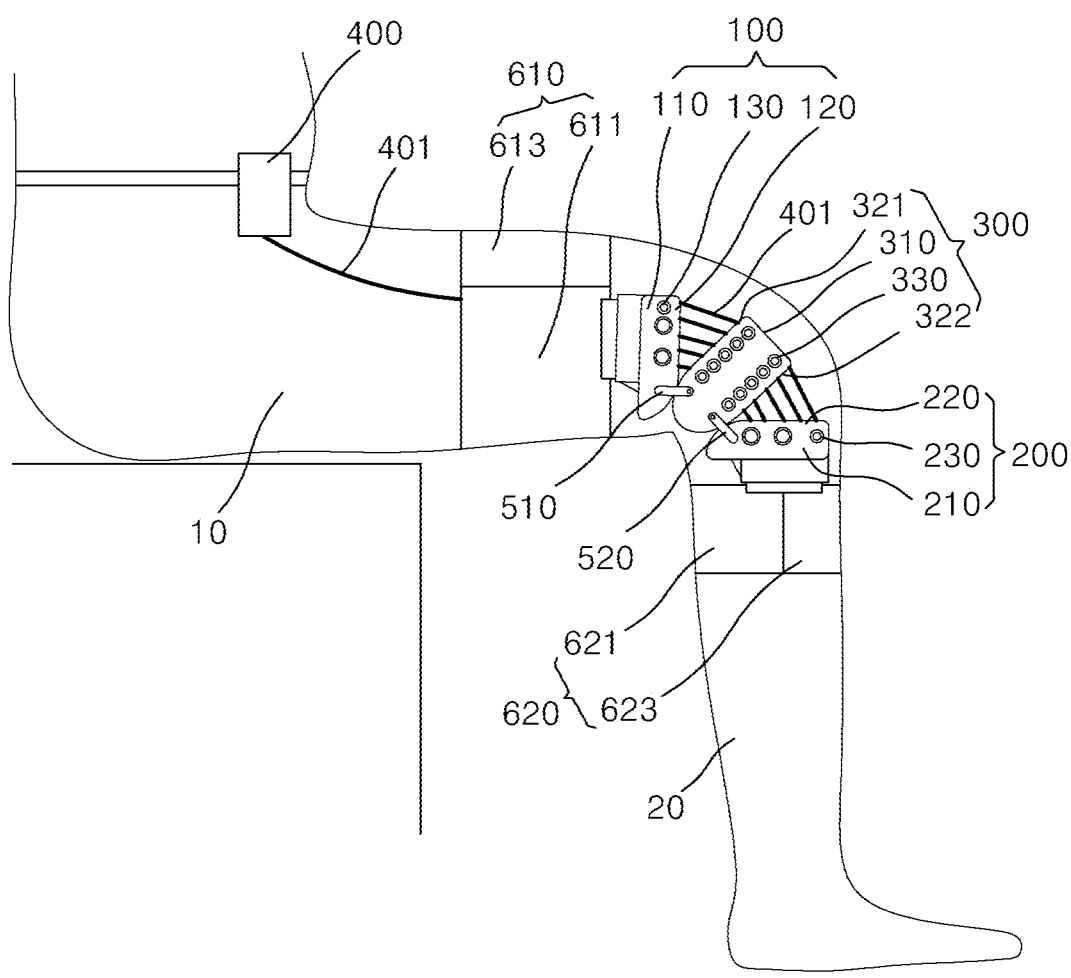
FIG. 1 is a perspective view illustrating a state in which a self-aligning joint assistance device according to a first embodiment of the present disclosure is worn on a leg.
Figure 2:
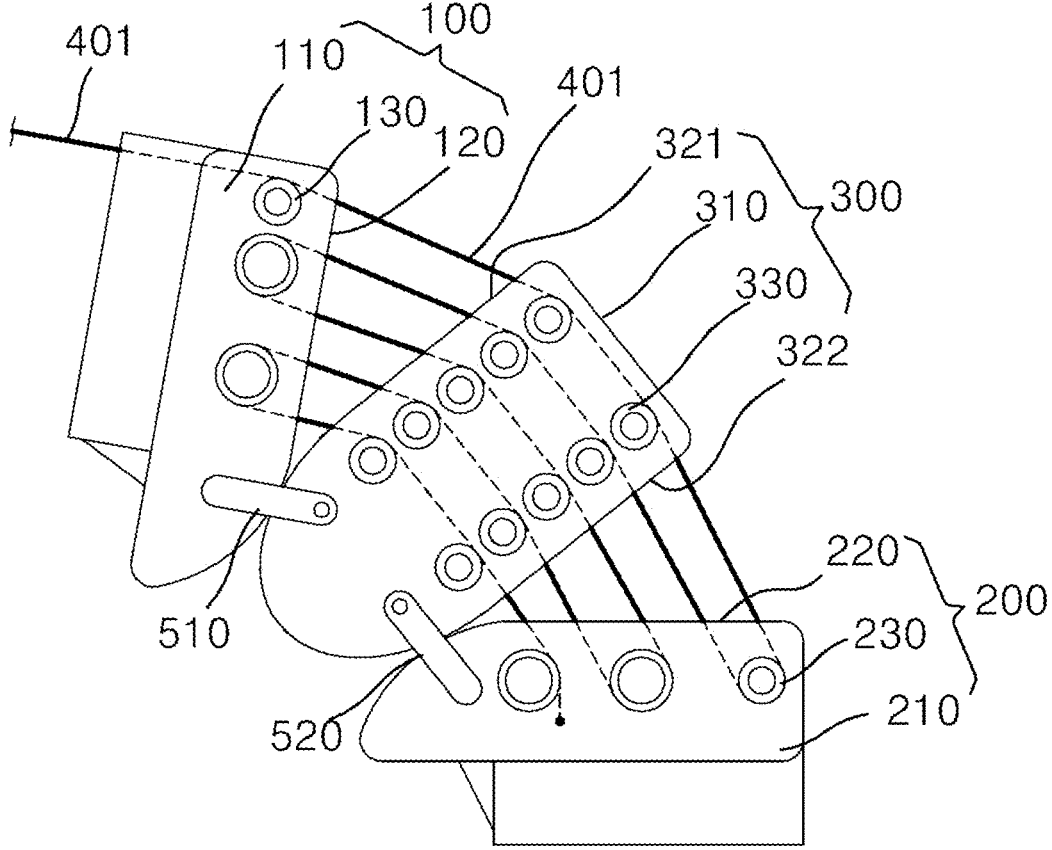
FIGS. 2 and 3 illustrate the operation of the self-aligning joint assistance device shown in FIG. 1.
Figure 3:
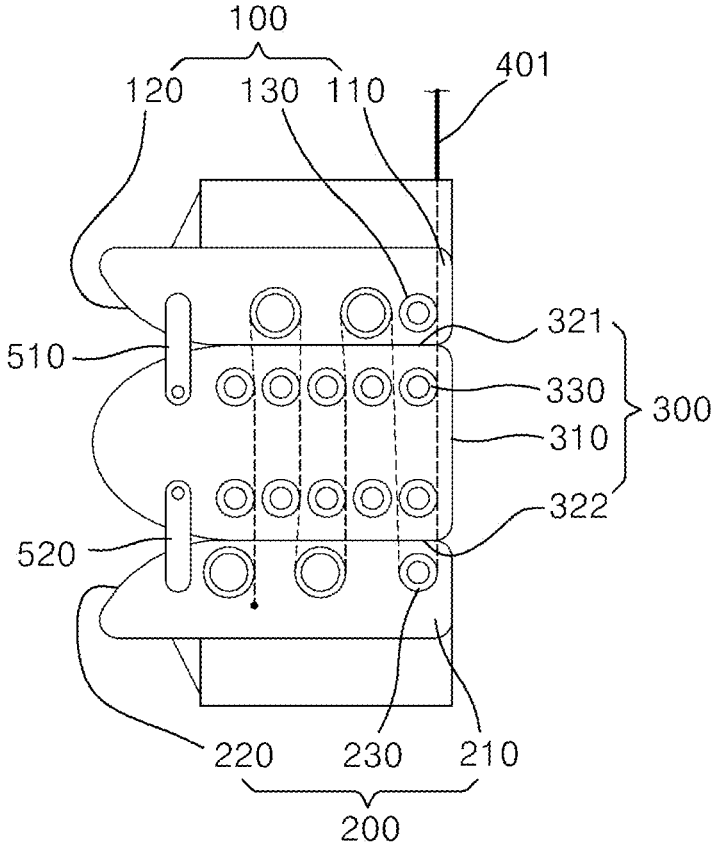

FIG. 1 is a perspective view illustrating a state in which a self-aligning joint assistance device according to a first embodiment of the present disclosure is worn, and FIGS. 2 and 3 illustrate the operation of the self-aligning joint assistance device shown in FIG. 1.

Referring to FIGS. 1 to 3, a self-aligning joint assistance device according to this embodiment includes a first member 100, a second member 200, an intermediate unit 300, and a wire 401.

The first member 100 is worn on and fixed to a first part 10 (or a thigh) by a first wearing member 610, and the second member 200 is worn on and fixed to a second part 20 (or a calf) of the user by a second wearing member 620. The intermediate unit 300 is disposed between the first member 100 and the second member 200, and the upper portion thereof contacts the first member 100 and the lower portion thereof contacts the second member 200.

The first member 100 includes a first body 110, a plurality of first rollers 130 and a first sliding portion 120. The first member 100 is plate-shaped to be in surface contact with a side of the first part 10. The plurality of first rollers 130 are disposed on the first body 110. The first sliding portion 120 is provided on the lower surface of the first body 110. That is, the first sliding portion 120 is provided on a portion of the first body 110 that is in contact with the intermediate unit 300. In this embodiment, the first sliding portion 120 has a convex shape and extends in the longitudinal direction. In addition, the first sliding portion 120 is provided with a curved surface that gradually curves away from the intermediate unit 300 toward the rear of the joint (i.e., the knee joint in this embodiment). The plurality of first rollers 130 are disposed within the first body 110 to be freely rotatable with respect to the first body 110, and are arranged in the front-rear direction of the knee.

The second member 200 is disposed below the first member 100 and is shaped to be approximately symmetrical to the first member 100. The second member 200 includes a second body 210, a plurality of second rollers 230, and a second sliding portion 220. The second member 200 is plate-shaped to be in surface contact with a side of the second part 20. The plurality of second rollers 230 are disposed on the second body 210. The second sliding portion 220 is provided on the upper surface of the second body 210. That is, the second sliding portion 220 is provided on a portion of the second body 210 that is in contact with the intermediate unit 300. In this embodiment, the second sliding portion 220 has a convex shape and extends in the longitudinal direction. In addition, the second sliding portion 220 is provided with a curved surface that gradually curves away from the intermediate unit 300 toward the rear of the joint. The plurality of second rollers 230 are disposed within the second body 210 to be freely rotatable with respect to the second body 210, and are arranged in the front-rear direction of the joint.

The intermediate unit 300 disposed between the first member 100 and the second member 200 includes an intermediate member 310, a first contact portion 321, a second contact portion 322, and a plurality of intermediate rollers 330. The intermediate member 310 is plate-shaped to be in surface contact with a side of the knee joint.

The first contact portion 321 is provided on the upper surface of the intermediate member 310. The first contact portion 321 is configured to allow mutual sliding while in contact with the first sliding portion 120 of the first member 100. In this embodiment, the first contact portion 321 has a concave shape corresponding to the convex shape of the first sliding portion 120. This configuration of the first sliding portion 120 and the first contact portion 321 allows the first member 100 and the intermediate member 310 to slide relative to each other without disengaging from each other while in contact with each other. The first contact portion 321 of the intermediate unit 300 is configured to include a curved surface that is shaped to be progressively more distant from the first member 100 toward the rear of the joint.

The second contact portion 322 is provided on the lower surface of the intermediate member 310. The second contact portion 322 is configured to allow mutual sliding while in contact with the second sliding portion 220 of the second member 200. In this embodiment, the second contact portion 322 has a concave shape corresponding to the convex shape of the second sliding portion 220. This configuration of the second sliding portion 220 and the second contact portion 322 allows the second member 200 and the intermediate member 310 to slide relative to each other while in contact with each other without disengaging from each other. The second contact portion 322 of the intermediate unit 300 is configured to include a curved surface that is shaped to be progressively more distant from the second member 200 toward the rear of the articulation.

The plurality of intermediate rollers 330 are disposed within the intermediate member 310 to be freely rotatable with respect to the intermediate member 310, and are arranged in the front-rear direction of the joint.

The first body 110 of the first member 100 and the intermediate member 310 of the intermediate unit 300 are connected by a first connecting member 510. The first connecting member 510 is in the form of a link connecting the first body 110 and the intermediate member 310. Accordingly, the first connecting member 510 connects the first member 100 and the intermediate unit 300 to each other to allow mutual sliding and rotation of the first body 110 and the intermediate member 310 on an identical plane while preventing lateral relative movement thereof.

The second body 210 of the second member 200 and the intermediate member 310 of the intermediate unit 300 are connected by a second connecting member 520. The second connecting member 520 is in the form of a link connecting the second body 210 of the second member 200 and the intermediate member 310 of the intermediate unit 300. Accordingly, the second connecting member 520 connects the second member 200 and the intermediate unit 300 to each other to allow mutual sliding and rotation of the second body 210 and the intermediate member 310 on an identical plane while preventing lateral relative movement thereof.

In this embodiment, the first connecting member 510 is formed of an elastic material that may be appropriately bent to allow relative tilting of the first member 100 and the intermediate member 310 within a predetermined angular range while not allowing lateral relative movement therebetween. The second connecting member 520 is also formed of an elastic material, like the first connecting member 510.

The wire 401 is disposed to pass through at least a portion of the plurality of first rollers 130, the plurality of intermediate rollers 330, and the plurality of second rollers 230 such that tension may be provided in a direction in which the first body 110, the intermediate unit 300, and the second member 200 approach each other. That is, the wire 401 is disposed to pass along various paths through the first rollers 130, the intermediate rollers 330, and the second rollers 230 of the first body 110, the intermediate member 310, and the second body 210, respectively, so that when the wire 401 is pulled and tensioned, the first body 110, the intermediate member 310, and the second body 210 slide toward each other and are aligned with each other at a position and in a direction in which the path of the wire 401 is shortest. Accordingly, the first rollers 130, the second rollers 230, and the wire 401 operate in the form of a movable pulley. That is, even a relatively small amount of tension applied to the wire 401 produces a force that may effectively assist the knee joint and assist the straightening of the knee joint. The intermediate rollers 330 serve to maintain the path of the wire 401.

In this embodiment, one end of the wire 401 is fixed to second body 210. The wire 401 passes alternately between the first and second rollers 130 and 230 in a zigzag path and is simultaneously guided and extended by the intermediate rollers 330 as shown in FIGS. 2 and 3. The other end of the wire 401 is connected to a driving unit 400. In this embodiment, the driving unit 400 is worn on the waist of the user to adjust the tension applied to the wire 401. The driving unit 400 may also be worn on and fixed to other parts, such as the first part 10, as desired. The driving unit 400 may be configured to pull the wire 401 using a motor, or may be configured to transmit tension to the wire 401 using an elastic member, such as a spring. The driving unit 400 may be provided in a variety of other configurations that may transmit tension to the wire 401.

The first wearing member 610, by which the first member 100 is worn on the first part 10, may be variously modified to have any structure capable of fixing the first member 100 to the first part 10. In this embodiment, the first wearing member 610 having the structure as shown in FIG. 1 is used. The first wearing member 610 of the self-aligning joint assistance device according to this embodiment includes a first wear support 611 and a first band 613. The first wear support 611 is coupled to the first member 100. The first wear support 611 is formed by bending a thin plate-shaped member formed of a synthetic resin material into a U-shape. The first band 613 is formed of an elastically-stretchable elastic material and is coupled to opposite ends of the first wear support 611. In this embodiment, the first wear support 611 is disposed to wrap around the rear of the first part 10, and the first band 613 is coupled to the opposite ends of the first wear support 611 to wrap around the front of the first part 10. With this configuration, the first wearing member 610, even though having a lightweight and simple structure, may enable the first member 100 to be worn on the first part 10 while effectively supporting the first part 10. In addition, the first wearing member 610 may be stably worn on the first part 10 without causing discomfort to the user, even in the case where the muscles of the first part 10 expand or contract as the knee joint moves.

The second wearing member 620, by which the second member 200 is worn on the second part 20, has a structure similar to that of the first wearing member 610. The second wearing member 620 includes a second wear support 621 and a second band 623. The second wear support 621 is coupled to the second member 200. The second wear support 621 is formed by bending a thin plate-shaped member formed of a synthetic resin material into a U-shape. The second band 623 is formed of an elastically-stretchable elastic material and is coupled to opposite ends of the second wear support 621. The second wear support 621 is disposed to wrap around the rear of the second part 20, and the second band 623 is coupled to the opposite ends of the second wear support 621 to wrap around the front of the second part 20.

Hereinafter, the operation of the self-aligning joint assistance device according to this embodiment configured as above will be described.

First, the first wearing member 610 is worn on the first part 10 and the second wearing member 620 is worn on the second part 20 so that the first wearing member 610 and the second wearing member 620 are in the same state as shown in FIG. 1.

When the tension is removed from the wire 401, the user is free to bend the knee joint. When the user performs a knee bending motion, such as sitting on a chair or sitting on the ground, the first member 100, the intermediate unit 300, and the second member 200 each move to perform relative movement and relative rotation in response to the movement of the knee joint, as shown in FIG. 2. Even in the case where the respective users wearing the self-aligning joint assistance device according to this embodiment have different lower body structures or motion characteristics, the first member 100, the intermediate unit 300, and the second member 200 move independently of each other with a high degree of freedom by adapting to the structure of the knee joint. Accordingly, when the wire 401 is not tensioned, the movement of the knee joint of the user is not resisted at all, and no discomfort is caused to the user.

In addition, as described above, the self-aligning joint assistance device according to this embodiment has a curved shape in which the first sliding portion 120 and the second sliding portion 220 each are progressively more distant from the intermediate unit 300 toward the rear of the knee, so that the first member 100 and the second member 200 rotate more smoothly in accordance with the angle of the knee joint when the knee joint is bent. The first contact portion 321 and the second contact portion 322 of the intermediate unit 300 also have a curved shape to be progressively more distant from the first member 100 and the second member 200, respectively, toward the rear of the knee so as to effectively perform the operation described above.

At this time, the wire 401 moves by passing through the first rollers 130, the intermediate rollers 330, and the second rollers 230 in response to the relative movement and the relative rotation of each of the first member 100, the intermediate unit 300, and the second member 200. When the wire 401 is unwound by the driving unit 400 with only a small amount of tension applied to the wire 401, the first member 100, the intermediate unit 300, and the second member 200 slide and adjust the position and direction relative to each other while remaining in contact with each other under the tension of the wire 401 and by the first connecting member 510 and the second connecting member 520.

Thereafter, when the driving unit 400 is operated to pull the wire 401, the tension on the wire 401 causes the first member 100, the intermediate unit 300, and the second member 200 to move toward each other, as shown in FIG. 3, thereby causing the knee to be straightened. When the wire 401 is pulled by the driving unit 400, the wire 401 rotates and moves the first rollers 130, the intermediate rollers 330, and the second rollers 230 to transmit a force in a direction in which the first member 100 and the second member 200 each move toward the intermediate unit 300 and the rotation angle decreases. At this time, the first member 100, the intermediate unit 300, and the second member 200 move in a direction of decreasing the distance and angle from each other while sliding and rotating relative to each other with a high degree of freedom in accordance with the body shape of the user. As a result, the knee joint of the user is straightened as shown. The femur and the lower leg are not connected to each other about a single axis of rotation but perform complex relative movements according to the body shape of each person based on the anatomical structure of the knee joint, wherein the self-aligning joint assistance device according to this embodiment assists the movement of the knee joint by automatic alignment of the respective components according to the posture and body shape of the user. Accordingly, the present disclosure may effectively assist the movement of the knee joint with minimal discomfort or foreign body sensation to the user.

In addition, as described above, because the wire 401 acts as a movable pulley while moving through the first rollers 130 and the second rollers 230, the knee joint movement may be assisted with a sufficiently strong force even in the case where the driving unit 400 does not pull the wire 401 with a strong force. That is, even in the case where the driving unit 400 used does not have a large power output, the knee joint movement may be easily assisted by the driving unit 400 as long as the driving unit 400 may pull the wire 401 with a sufficient operating displacement. Therefore, the driving unit 400 may be reduced in size and weight. As a result, the self-aligning joint assistance device according to the present invention may be fabricated at a relatively low cost.

As described above, the first rollers 130 and the second rollers 230 serve to cause the wire 401 to act on movable pulleys, and the intermediate rollers 330 serve to maintain the wire 401 along the path within the intermediate unit 300 while preventing the wire 401 from deviating from the intermediate unit 300.

Each of the first wear support 611 and the second wear support 621 may be implemented using a thin sheet formed of a synthetic resin material, as described above, and thus may be manufactured to be lightweight and inexpensive. Even such thin plate-shaped members have a sufficient stiffness in the longitudinal direction of the first part 10 or the second part 20 when bent into a U-shape. Accordingly, the first wear support 611 and the second wear support 621 wrap around and support the backs of the first part 10 and the second part 20, respectively, and when the wire 401 is pulled to apply a force to the first member 100 and the second member 200, respectively, in the direction in which the knee is straightened, the first wear support 611 and the second wear support 621 effectively transmit the force to the first part 10 and the second part 20, respectively.

In addition, the first band 613 and the second band 623 are each formed of an elastic material, thereby allowing the first wearing member 610 and the second wearing member 620 to closely fit to the outer diameter sizes of the first part 10 and the second part 20, respectively, and to remain in a worn state. Unlike other conventional wearing members having a fixed inner diameter size, the first wearing member 610 and the second wearing member 620 may remain worn while contracting and expanding according to the outer diameter sizes that change with the contraction and expansion of the muscles of the first part 10 and the second part 20, respectively, thereby effectively assisting the movement of the knee joint while providing comfort to the user.

The present disclosure has been described above with reference to example embodiments, but the scope of the present disclosure is not limited to the forms described and illustrated above.

For example, a case where one end of the wire 401 is fixed to the first member 100 and the other end of the wire 401 is connected to the driving unit 400 has been described above as an example, the self-aligning joint assistance device of the present disclosure may be configured such that the opposite ends of the wire are connected to the driving unit and are pulled or unwound simultaneously. The wire may also be configured such that that one end is connected to the first member or the intermediate unit rather than the second member and the other end is connected to the driving unit.

The path of the wire 401 may also be varied as desired. The wire 401 may be disposed to pass through the first member 100, the intermediate unit 300, and the second member 200 along various paths other than those shown in FIGS. 2 and 3. Once the wire is disposed to pass through the first roller, the intermediate roller, and the second roller, the operation as described above may be realized.

In some cases, when the wire 401 is connected to pass through each of the first member 100, the intermediate unit 300, and the second member 200 at least once, the operation and effects of the present disclosure as described above may be achieved even in the case where at least one of the first rollers 130, the intermediate rollers 330, and the second rollers 230 is not provided.

The number of each of the driving unit 400 and the wire 401 is not limited to one, and may be varied as desired. In other words, the self-aligning joint assistance device of the present disclosure may be configured to include a plurality of wires. In this case, the self-aligning joint assistance device of the present disclosure may be configured such that the plurality of wires are connected to a single driving unit to be pulled or unwound or each wire is connected to a separate driving unit for to be pulled or unwound.

The driving unit 400 may be fixed to a human body part, such as the waist of the user, or may be disposed on the first wearing member 610 or the second wearing member 620. In some cases, the self-aligning joint assistance device of the present disclosure may be implemented so as not to include the driving unit 400. In this case, the self-aligning joint assistance device of the present disclosure that does not include the driving unit 400 may be produced and sold, and the user may use the self-aligning joint assistance device of the present disclosure by connecting the wire 401 to the prepared driving unit 400.

In addition, the shapes of the first member 100, the intermediate unit 300, the second member 200, the first wearing member 610, and the second wearing member 620 are not limited to the shapes shown in the figures, but may be varied. That is, the first member, the intermediate unit, and the second member may each be modified to have various polygons or curved surfaces. The shapes of the first sliding portion, the second sliding portion, the first contact portion, and the second contact portion may also be varied depending on such shapes of the first member, the intermediate unit, and the second member. In particular, the first sliding portion and the intermediate unit may be configured such that the first sliding portion and the first contacting portion are not in full contact but are in contact only at some points. The same applies to the relationship between and the shapes of the second sliding portion and the second contact portion.

In addition, the concave and convex shapes of the first sliding portion 120, the second sliding portion 220, the first contact portion 321, and the second contact portion 322 may be varied into various other shapes, and in some cases, the shape of each of the first sliding portion, the second sliding portion, the first contact portion, and the second contact portion may be varied into a shape that does not include the concave or convex portion. In some cases, the first sliding portion, the second sliding portion, the first contacting portion, and the second contacting portion may be configured such that the mutual contact surfaces include a guide groove extending in the longitudinal direction and a guide protrusion slidably inserted into the guide groove, respectively.

The self-aligning joint assistance device may also be configured with a structure in which none of the first sliding portion 120, the second sliding portion, the first contact portion, and the second contact portion is provided with the curved surface as described above. The shapes of the first member 100, the second member 200, and the intermediate unit 300 may be varied, and when the knee is straightened and the first member 100, the intermediate unit 300, and the second member 200 are closest to each other due to the smallest gap therebetween, the tension of the wire 401 causes the first member 100, the intermediate unit 300, and the second member 200 to automatically align with each other to assist the knee joint while being adjusted in position and direction. In some cases, the shapes of the first member, the intermediate unit, and the second member may be adjusted so that the first member, the intermediate unit, and the second member are in an aligned position when the knee is bent at a predetermined angle rather than fully straightened.

The self-aligning joint assistance device of the present disclosure may also be implemented such as not to include the first connecting member 510 or the second connecting member 520 as described above. The self-aligning joint assistance device may also be configured to include the first connecting member and the second connecting member having a shape and structure different from those described and illustrated above.

Next, a self-aligning joint assistance device according to a second embodiment of the present disclosure will be described with reference to FIG. 3. The self-aligning joint assistance device according to the second embodiment differs from the self-aligning joint assistance device according to the first embodiment in that the structure of the intermediate unit is different, but all other components are the same. Accordingly, the remaining components except for the intermediate unit are shown by assigning the same reference numerals as in the self-aligning joint assistance device according to the first embodiment, and detailed descriptions thereof are omitted.

Figure 4:
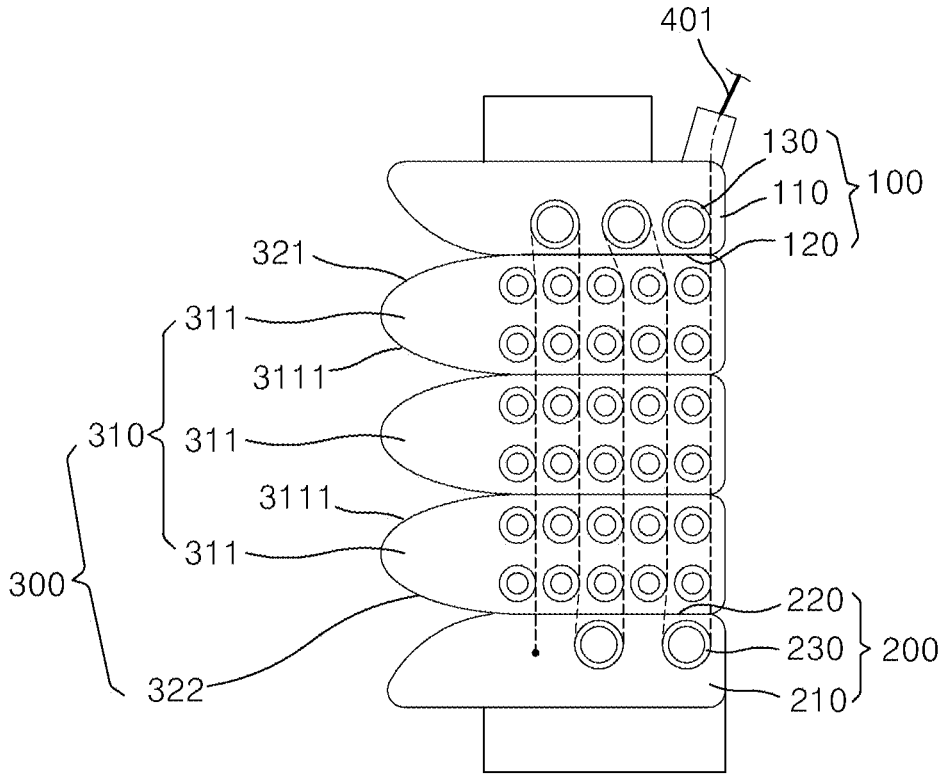
FIG. 4 is a plan view illustrating a self-aligning joint assistance device according to a second embodiment of the present disclosure.

The intermediate member 310 of the self-aligning joint assistance device according to the second embodiment is characterized by including a plurality of intermediate bodies 311. The intermediate member 310 of the self-aligning joint assistance device according to the first embodiment is formed as a single component, but the intermediate member of the self-aligning joint assistance device according to the second embodiment includes three intermediate bodies 311, as shown in FIG. 4. The intermediate bodies 311 include intermediate contact portions 3111 to allow sliding while in contact with adjacent intermediate bodies 311. Mutual contact portions of the intermediate bodies 311 are formed into the intermediate contact portions 3111 and are configured to allow mutual sliding with respect to each other.

The intermediate bodies 311 are each provided with at least one intermediate roller 330.

Except for this configuration of the intermediate member 310 of the intermediate unit 300, the configuration and the operating relationship of the self-aligning joint assistance device according to the second embodiment are the same as those of the self-aligning joint assistance device according to the first embodiment.

In the self-aligning joint assistance device of this embodiment configured as above, when the wire 401 is pulled or unwound, the first member 100, the intermediate unit 300, and the second member 200 slide with respect to each other and change the positions and directions in response to the movement of the knee joint, as in the first embodiment. In addition, in this embodiment, as the intermediate members 310 of the intermediate unit 300 also slide with respect to each other, the positions and angles thereof are adjusted by the tension of the wire 401. The intermediate members 310 are connected to each other by the wire 401 to remain in contact with each other under tension while the positions and directions thereof are adjusted in response to the movement of the joint.

The components of the self-aligning joint assistance device according to the second embodiment may be varied as in the self-aligning joint assistance device according to the first embodiment described above.

Figure 5:
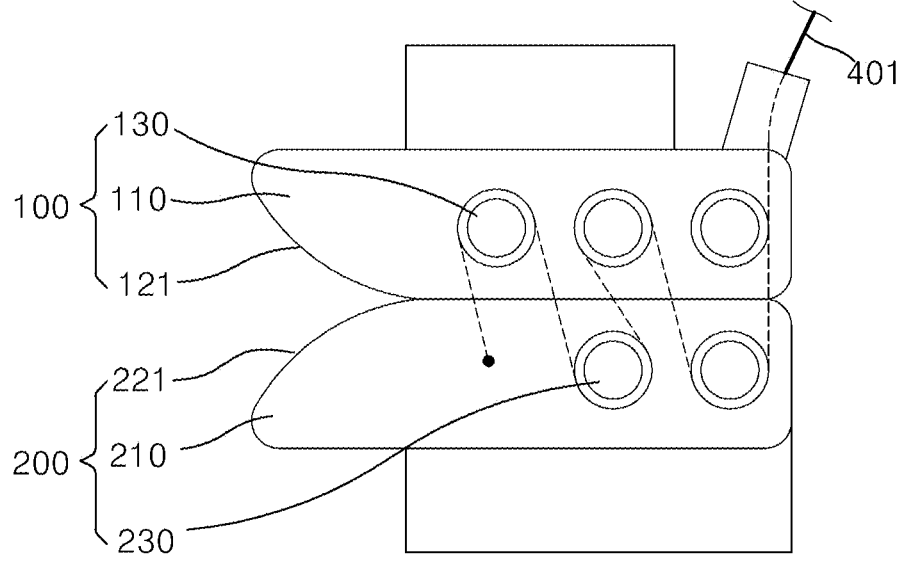
FIG. 5 is a plan view illustrating a self-aligning joint assistance device according to a third embodiment of the present disclosure.

Next, a self-aligning joint assistance device according to a third embodiment of the present disclosure will be described with reference to FIG. 5. Hereinafter, the same components as in the first embodiment will be shown and described by assigning the same reference numerals.

The self-aligning joint assistance device of the third embodiment is characterized by not including the intermediate unit 300. Components the same as or similar to those of the self-aligning joint assistance device according to the first embodiment are shown by assigning the same reference numerals, and detailed descriptions thereof are omitted.

The self-aligning joint assistance device of the third embodiment is configured such that the intermediate unit 300 is absent, and the first member 100 and the second member 200 slide and move relative to each other while in direct contact with each other. Accordingly, the first sliding portion 121 of the first member 100 and the second sliding portion 221 of the second member 200 slide and move relative to each other while in contact with each other. The first member 100 and the second member 200 are connected to each other by the wire 401, which transmits tension in a direction in which the first member 100 and the second member 200 approach each other while moving through the first rollers 130 of the first member 100 and the second rollers 230 of the second member 200.

When the tension of the wire 401 decreases and the wire 401 is unwound, the first member 100 and the second member 200 move in a direction away from each other and increase the angle therebetween. In contrast, when the wire 401 is pulled by the driving unit 400, the tension of the wire 401 causes the first member 100 and the second member 200 to move in a direction toward each other and decrease the angle therebetween.

To further facilitate such movement between the first member 100 and the second member 200, the first sliding portion 121 and the second sliding portion 221 may be provided with curved surfaces that are shaped to be progressively more distant from each other toward the rear of the joint. In addition, to guide mutual sliding, the first sliding portion 121 and the second sliding portion 221 may be configured such that one of the first and second sliding portions 121 and 221 is concave and the other of the first and second sliding portions 121 and 221 is convex or one of the first and second sliding portions 121 and 221 is provided as a recess and the other of the first and second sliding portions 121 and 221 is provided as a protrusion to be inserted into the recess to move therein.

In addition, similar to the first connecting member 510 and the second connecting member 520 of the first embodiment, a configuration of connecting members connecting the first member 100 and the second member 200 may be selectively provided.

As set forth above, cases where the present disclosure is used in the knee joint have been described primarily as examples hereinabove; however, the present disclosure may also be implemented and used in various other joints of the human body.

What is claimed is:

1. A self-aligning joint assistance device that is configured to be worn near a joint connecting a first part and a second part of a human body to assist movement of the joint, the joint assistance device comprising:

a first member configured to be worn on the first part, and comprising a first body, a plurality of first rollers disposed on the first body, and a first sliding portion provided on a lower surface of the first body;

a second member configured to be worn on the second part, and comprising a second body, a plurality of second rollers disposed on the second body, and a second sliding portion provided on an upper surface of the second body;

an intermediate unit disposed between the first member and the second member, and comprising an intermediate member disposed between the first member and the second member, a first contact portion provided on the intermediate member to allow mutual sliding while in contact with the first sliding portion of the first member, a second contact portion provided on the intermediate member to allow mutual sliding while in contact with the second sliding portion of the second member, and a plurality of intermediate rollers disposed on the intermediate member; and a wire disposed to pass through at least a portion of the plurality of first rollers, the plurality of intermediate rollers, and the plurality of second rollers to provide tension in a direction in which the first member, the intermediate unit, and the second member approach each other so that the first member, the intermediate unit, and the second member mutually slide and are aligned.

2. The joint assistance device of claim 1, wherein the first sliding portion and the first contact portion are shaped to correspond to each other in a longitudinal direction to guide mutual sliding, with one thereof being concave and the other thereof being convex, and the second sliding portion and the second contact portion are shaped to correspond to each other in a longitudinal direction to guide mutual, with one thereof being concave and the other thereof being convex.

3. The joint assistance device of claim 1, wherein the first sliding portion of the first member comprises a curved surface shaped to be progressively more distant from the intermediate unit toward a rear of the joint, and the second sliding portion of the second member comprises a curved surface shaped to be progressively more distant from the intermediate unit toward the rear of the joint.

4. The joint assistance device of claim 3, wherein the first contact portion of the intermediate unit comprises a curved surface shaped to be progressively more distant from the first member toward the rear of the joint, and the second contact portion of the intermediate unit comprises a curved surface shaped to be progressively more distant from the second member toward the rear of the joint.

5. The joint assistance device of claim 1, wherein the first contact portion of the intermediate unit comprises a curved surface shaped to be progressively more distant from the first member toward a rear of the joint, and the second contact portion of the intermediate unit comprises a curved surface shaped to be progressively more distant from the second member toward the rear of the joint.

6. The joint assistance device of claim 1, further comprising:

a first connecting member connecting the first body of the first member and the intermediate member of the intermediate unit to each other to allow mutual sliding and rotation of the first body and the intermediate member on an identical plane while preventing lateral relative movement thereof; and a second connecting member connecting the second body of the second member and the intermediate member of the intermediate unit to each other to allow mutual sliding and rotation of the second body and the intermediate member on an identical plane while preventing lateral relative movement thereof.

7. The joint assistance device of claim 1, wherein the intermediate member of the intermediate unit comprises a plurality of intermediate bodies sequentially disposed to be adjacent to each other, each of the plurality of intermediate bodies comprising an intermediate contact portion shaped to allow sliding while in contact with another adjacent intermediate body among the plurality of intermediate bodies, and at least one intermediate roller among the plurality of intermediate rollers of the intermediate unit is disposed on each of the plurality of intermediate bodies.

8. The joint assistance device of claim 1, further comprising:

a first wearing member by which the first member is configured to be worn on the first part; and a second wearing member by which the second member is configured to be worn on the second part.

9. The joint assistance device of claim 8, wherein the first wearing member comprises a first wear support that is a plate-shaped member bent into a U-shape and coupled to the first member and a first band formed of an elastic material and coupled to opposite ends of the first wear support and configured to elastically wrap around the first part, and the second wearing member comprises a second wear support that is a plate-shaped member bent into a U-shape and coupled to the second member and a second band formed of an elastic material and coupled to opposite ends of the second wear support and configured to elastically wrap around the second part.

10. The joint assistance device of claim 1, further comprising a driving unit connected to the wire and configured to provide tension to the wire, wherein one end of the wire is connected to the driving unit and the other end of the wire is fixed to one of the first body, the intermediate member, and the second body.

11. The joint assistance device of claim 1, further comprising a driving unit connected to the wire and configured to provide tension to the wire, wherein opposite ends of the wire are connected to the driving unit.

12. A self-aligning joint assistance device that is configured to be worn near a joint connecting a first part and a second part of a human body to assist movement of the joint, the joint assistance device comprising:

a first member configured to be worn on the first part, and comprising a first body, a plurality of first rollers disposed on the first body, and a first sliding portion provided on a lower surface of the first body;

a second member configured to be worn on the second part, and comprising a second body, a plurality of second rollers disposed on the second body, and a second sliding portion provided on an upper surface of the second body and configured to allow mutual sliding while in contact with the first sliding portion of the first member; and a wire disposed to pass through at least a portion of the plurality of first rollers and the plurality of second rollers to provide tension in a direction in which the first member and the second member approach each other so that the first member and the second member mutually slide and are aligned.

13. The joint assistance device of claim 12, wherein the first sliding portion and the second sliding portion are shaped to correspond to each other in a longitudinal direction to guide mutual sliding, with one thereof being concave and the other thereof being convex.

14. The joint assistance device of claim 12, wherein the first sliding portion of the first member comprises a curved surface shaped to be progressively more distant from the second member toward a rear of the joint.

15. The joint assistance device of claim 12, wherein the second sliding portion of the second member comprises a curved surface shaped to be progressively more distant from the first member toward a rear of the joint.

16. The joint assistance device of claim 12, further comprising a connecting member connecting the first body of the first member and the second body of the second member to each other to allow mutual sliding and rotation of the first body and the second body on an identical plane while preventing lateral relative movement thereof.

17. The joint assistance device of claim 12, further comprising:

a first wearing member by which the first member is configured to be worn on the first part; and a second wearing member by which the second member is configured to be worn on the second part.

18. The joint assistance device of claim 17, wherein the first wearing member comprises a first wear support that is a plate-shaped member bent into a U-shape and coupled to the first member and a first band formed of an elastic material and coupled to opposite ends of the first wear support and configured to elastically wrap around the first part, and the second wearing member comprises a second wear support that is a plate-shaped member bent into a U-shape and coupled to the second member and a second band formed of an elastic material and coupled to opposite ends of the second wear support and configured to elastically wrap around the second part.

19. The joint assistance device of claim 12, further comprising a driving unit connected to the wire and configured to provide tension to the wire, wherein one end of the wire is connected to the driving unit and the other end of the wire is fixed to one of the first body and the second body.

20. The joint assistance device of claim 12, further comprising a driving unit connected to the wire and configured to provide tension to the wire, wherein opposite ends of the wire are connected to the driving unit.

* * * * *